(12) United States Patent
Parramon et al.

(10) Patent No.: US 8,583,262 B2
(45) Date of Patent: Nov. 12, 2013

(54) IMPLANTABLE MEDICAL DEVICE THAT USES ELECTRICAL CURRENT STEERING BY MEANS OF OUTPUT IMPEDANCE MODULATION

(75) Inventors: Jordi Parramon, Valencia, CA (US); David K. L. Peterson, Valencia, CA (US); Kerry Bradley, Glendale, CA (US); Rafael Carbunaru, Valley Village, CA (US); Andrew DiGiore, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 792 days.

(21) Appl. No.: 12/606,065

(22) Filed: Oct. 26, 2009

(65) Prior Publication Data
US 2010/0125315 A1 May 20, 2010

Related U.S. Application Data

(60) Provisional application No. 61/114,959, filed on Nov. 14, 2008.

(51) Int. Cl.
*A61N 1/08* (2006.01)
(52) U.S. Cl.
USPC ............................................. 607/148; 607/68
(58) Field of Classification Search
USPC ...................................................... 607/68, 148
See application file for complete search history.

(56) References Cited

U.S. PATENT DOCUMENTS

| | | | |
|---|---|---|---|
| 3,895,639 A * | 7/1975 | Rodler ............................. | 607/67 |
| 4,050,004 A * | 9/1977 | Greatbatch ...................... | 363/59 |
| 4,121,593 A * | 10/1978 | Kastrubin et al. .............. | 607/46 |
| 5,233,985 A * | 8/1993 | Hudrlik .......................... | 607/27 |
| 6,181,969 B1 | 1/2001 | Gord | |
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 7,239,920 B1 | 7/2007 | Thacker et al. | |
| 7,317,948 B1 | 1/2008 | King et al. | |
| 7,389,140 B1 | 6/2008 | Kroll | |
| 7,539,538 B2 | 5/2009 | Parramon et al. | |
| 8,131,357 B2 | 3/2012 | Bradley et al. | |

(Continued)

FOREIGN PATENT DOCUMENTS

WO WO 2005/101661 A1 10/2005

OTHER PUBLICATIONS

PCT International Search Report for PCT/US2009/062115, Applicant: Boston Scientific Neuromodulation Corporation, Form PCT/ISA/210 and 220, dated Apr. 23, 2010 (9 pages).
PCT Written Opinion of the International Search Authority for PCT/US2009/062115, Applicant: Boston Scientific Neuromodulation Corporation, Form PCT/ISA/237, dated Apr. 23, 2010 (7 pages).

(Continued)

*Primary Examiner* — Christopher D Koharski
*Assistant Examiner* — Natasha Patel
(74) *Attorney, Agent, or Firm* — Vista IP Law Group LLP

(57) ABSTRACT

A method and system of providing therapy to a patient implanted with an array of electrodes is provided. Electrical stimulation current is conveyed from at least two of the electrodes to at least one of the electrodes along at least two electrical paths through tissue of the patient, and the electrical stimulation current is shifted between the electrical paths by actively adjusting one or more finite resistances respectively associated with one or more of the electrical paths.

31 Claims, 13 Drawing Sheets

(56) References Cited

U.S. PATENT DOCUMENTS

| | | |
|---|---|---|
| 2003/0139781 A1 | 7/2003 | Bradley et al. |
| 2004/0034394 A1 | 2/2004 | Woods et al. |
| 2005/0245977 A1* | 11/2005 | Varrichio et al. ............... 607/11 |
| 2005/0267546 A1* | 12/2005 | Parramon et al. ............... 607/48 |
| 2006/0224222 A1 | 10/2006 | Bradley et al. |
| 2007/0100399 A1 | 5/2007 | Parramon et al. |
| 2007/0208394 A1 | 9/2007 | King et al. |
| 2010/0023069 A1 | 1/2010 | Moffitt et al. |

OTHER PUBLICATIONS

PCT International Preliminary Report on Patentability (Chapter I of the Patent Cooperation Treaty) for PCT/US2009/062115, Applicant: Boston Scientific Neuromodulation Corporation, Form PCT/IB/326 and 373, dated May 26, 2011 (6pages).

U.S. Appl. No. 61/083,491, System and Method for Maintaining a Distribution of Currents in an Electrode Array Using Independent Voltage Sources, Inventor: Michael Moffitt, et al., filed Jul. 24, 2008.

* cited by examiner

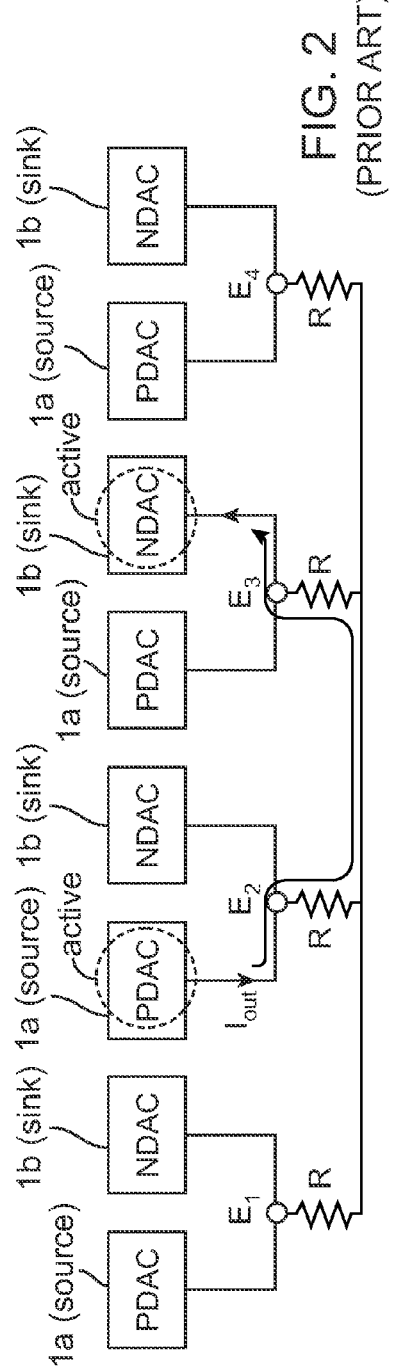
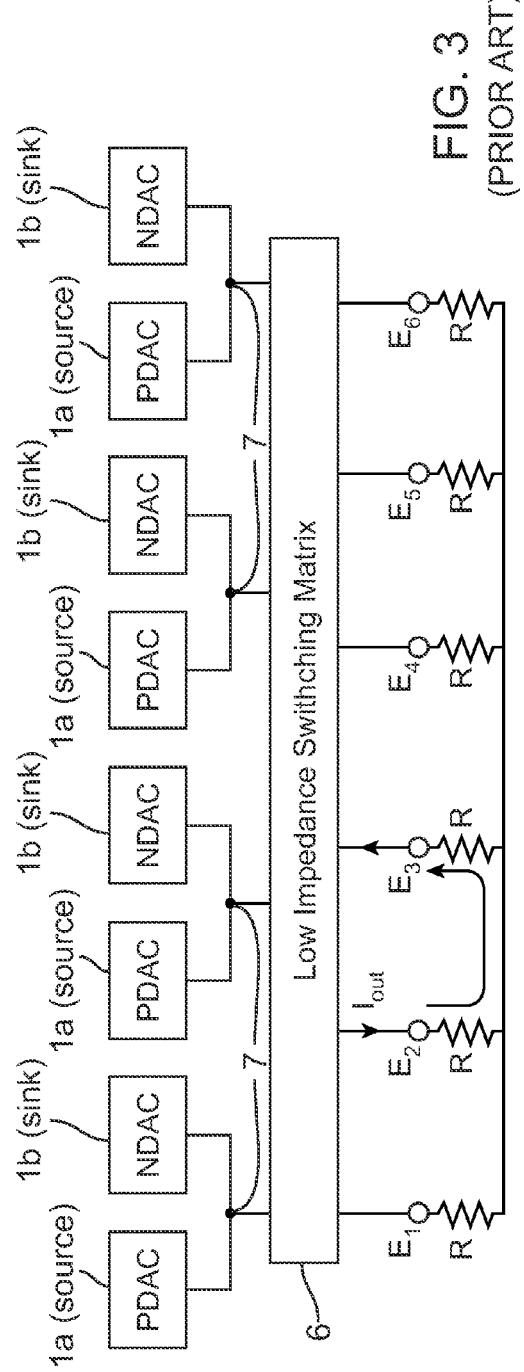
FIG. 2 (PRIOR ART)
FIG. 3 (PRIOR ART)

IMPLANTABLE MEDICAL DEVICE THAT USES ELECTRICAL CURRENT STEERING BY MEANS OF OUTPUT IMPEDANCE MODULATION

RELATED APPLICATION

The present application claims the benefit under 35 U.S.C. §119 to U.S. provisional patent application Ser. No. 61/114,959, filed Nov. 14, 2008. The foregoing application is hereby incorporated by reference into the present application in its entirety.

FIELD OF THE INVENTION

The present invention relates to tissue stimulation systems, and more particularly, to a system and method for steering electrical current between stimulation electrodes.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. However, the number of electrodes available, combined with the ability to generate a variety of complex stimulation pulses, presents a huge selection of stimulation parameter sets to the clinician or patient.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the stimulation region or areas correlating to the pain. Such programming ability is particularly advantageous for targeting the tissue during implantation, or after implantation should the leads gradually or unexpectedly move that would otherwise relocate the stimulation energy away from the target site. By reprogramming the neurostimulator (typically by independently varying the stimulation energy on the electrodes), the stimulation region can often be moved back to the effective pain site without having to re-operate on the patient in order to reposition the lead and its electrode array. When adjusting the stimulation region relative to the tissue, it is desirable to make small changes in the proportions of current, so that changes in the spatial recruitment of nerve fibers will be perceived by the patient as being smooth and continuous and to have incremental targeting capability.

Electrical stimulation energy may be delivered from the neurostimulator to the electrodes using one or more current-controlled sources for providing stimulation pulses of a specified and known current (i.e., current regulated output pulses), or one or more voltage-controlled sources for providing stimulation pulses of a specified and known voltage (i.e., voltage regulated output pulses).

For example, with reference to FIG. 1, a neurostimulator may have multiple output current sources 1a and multiple current sinks 1b (only one current source 1a and one current sink 1b shown in FIG. 1) that are configured to supply/receive stimulating current to/from the electrodes $E_x$, $E_y$, and ultimately to/from tissue (represented by load 5 having a resistance R). The source 1a and sink 1b are sometimes respectively referred to as PDACs and NDACs, reflecting the fact that the source 1a is typically formed of P-type transistors, while the sink 1b is typically formed of N-type transistors. The use of transistors of these polarities is sensible given that the source 1a is biased to a high voltage (V+), where P-type transistors are most logical, while the sink 1b is biased to a low voltage (V−), where N-type transistors are most logical, as shown in FIG. 1. A suitable current generator is disclosed in U.S. Pat. No. 6,181,969 ("the '969 patent"), which is expressly incorporated herein by reference in its entirety.

The output current source 1a and output current sink 1b respectively include current generators 2a, 2b each configured to generate a reference current $I_{ref}$, and digital-to-analog converter (DAC) circuitry 3a, 3b configured for regulating/amplifying the reference current $I_{ref}$ provided by the current generators 2a, 2b, and delivering output current $I_{out}$ to the load 5 (having a resistance R). Specifically, the relation between $I_{out}$ and $I_{ref}$ is determined in accordance with input bits arriving on busses 4a, 4b, which respectively give the output current source 1a and output current sink 1b their digital-to-analog functionality. In accordance with the values of the various M bits on busses 4a, 4b any number of output stages (i.e., transistors M1, M2) are tied together in parallel such that $I_{out}$ can range from $I_{ref}$ to $2^M * I_{ref}$.

As shown in FIG. 1 for simplicity, the current source 1a is coupled to an electrode $E_x$, while the current sink 1b is coupled to a different electrode $E_y$. However, each electrode may actually be hard-wired to both the current source 1a and the current sink 1b, only one (or neither) of which is activated at a particular time to allow the electrode to selectively be used as either a source or sink (or as neither).

This architecture is shown in FIG. 2, which shows four exemplary electrodes $E_1$, $E_2$, $E_3$, and $E_4$, each having its own dedicated and hard-wired current source 1a and current sink 1b. Thus, an output current source 1a may be associated with electrode $E_2$ (e.g., $E_x$ of FIG. 1) at a particular point in time, while an output current sink 1b may be associated with electrode $E_3$ (e.g., $E_y$ of FIG. 1) at that time. At a later time, electrodes $E_2$ and $E_3$ could be switched, such that $E_2$ now operates as the sink, while electrode $E_3$ operates as the source, or new sources or sinks could be selected, etc.

Another architecture, shown in FIG. 3, uses a plurality of current sources 1a and sinks 1b, and further uses a low impedance switching matrix 6 that intervenes between the sources/sinks and the electrodes $E_x$. Each source/sink pair is hard-wired together at common nodes 7, such that the switching matrix 6 intervenes between the nodes 7 and the electrodes. Of course, only one of the source or the sink in each pair is activated at one time, and thus the node 7 in any pair will source or sink current at any particular time. Through appropriate control of the switching matrix 6, any of the nodes 7 may be connected to any of the electrodes $E_x$ at any time.

Further details discussing various architectures of current source/sink circuitry are provided in U.S. Patent Publication No. 2007/0100399, which is expressly incorporated herein by reference.

Because each current source and current sink requires a relatively large number of switches, it can be appreciated that as the number of current sources and current sinks increases, the complexity and space required to accommodate them increases. It is, thus, desirable to minimize the number of current sources/sinks needed, while still allowing the steering of electrical current between the electrodes.

SUMMARY OF THE INVENTION

In accordance with a first aspect of the present inventions, a method of providing therapy to a patient implanted with a plurality of electrodes is provided. The method comprises conveying electrical stimulation current from at least two of the electrodes to at least one of the electrodes along at least two electrical paths through tissue of the patient. The electrical stimulation current may either be cathodic or anodic.

The method further comprises shifting the electrical stimulation current between the electrical paths by actively adjusting one or more finite resistances respectively associated with one or more of the electrical paths. In one method, a single finite resistance is associated with only one of the electrical paths, and in another method, multiple finite resistances are respectively associated with the electrical paths. The electrical stimulation current may be generated by, e.g., a single current source, in which case, the magnitude of the electrical stimulation current generated by the current source may be adjusted to globally adjust the current flowing through the electrical paths.

An optional method comprises transcutaneously transmitting a control signal, thereby actively adjusting the finite resistance(s). In one example, the control signal may designate magnitude values (e.g., fractionalized current values) for the electrical stimulation current respectively along the electrical paths. The finite resistance(s) may then be adjusted to set the electrical stimulation current in the electrical paths respectively to the magnitude values. In another example, control signal designates one or more resistance values. The finite resistance(s) may then be adjusted to the designated resistance value(s).

Another optional method comprises measuring one or more electrical parameters (e.g., magnitudes of current in the electrical path(s) or impedances in the electrical path(s)) respectively associated with one or more of the electrical paths. In this case, the finite resistance(s) are adjusted in response to the measured electrical parameter(s). Still another optional method comprises determining at least one stimulator parameter in accordance with which the conveyed electrical stimulation current provides effective therapy to the patient, and programming an implanted neurostimulator with the stimulation parameter.

In accordance with a second aspect of the present inventions, a neurostimulation system is provided. The neurostimulation system comprises a plurality of electrical terminals configured for being respectively coupled to a plurality of electrodes. The neurostimulation system further comprises analog output circuitry configured for conveying electrical stimulation current between at least two of the electrical terminals to at least another of the electrical terminals through tissue.

The analog output circuitry includes one or more variable resistors respectively coupled to one or more of the electrical terminals. In one embodiment, the analog output circuitry further comprises a current source configured for generating the electrical stimulation current. In this case, the control circuitry may be configured for modifying the total magnitude of the electrical stimulation current generated by the current source. In one embodiment, a single variable resistor is coupled to only one of the electrical terminals, and in another embodiment, multiple variable resistors are respectively coupled to the electrical terminals. The neurostimulation system further comprises control circuitry configured for adjusting the variable resistor(s), thereby modifying the magnitudes of the electrical stimulation current at the electrical terminal(s). In one embodiment, the neurostimulation system further comprises a housing containing the plurality of electrical terminals, analog output circuitry, and control circuitry.

In an optional embodiment, the neurostimulation system further comprises telemetry circuitry configured for wirelessly receiving a control signal, and the control circuitry is configured for adjusting the variable resistor(s) in response to the control signal. In one embodiment, the control signal designates at least two magnitude values (e.g., fractionalized current values) for the electrical stimulation current at the least two electrical terminals, and wherein the one or more variable resistors are adjusted to set the electrical stimulation current at the electrical terminal(s) respectively to the magnitude values. In another optional embodiment, the control signal designates one or more resistance values respectively for the variable resistor(s), and the control circuitry is configured for adjusting the variable resistor(s) respectively to the resistance value(s).

In another optional embodiment, the neurostimulation system further comprises monitoring circuitry configured for measuring one or more electrical parameters (e.g., the magnitudes of current at the electrical terminal(s) or impedances at the electrical terminal(s)) respectively associated with one or more of the electrical terminal(s), and the control circuitry is configured for adjusting the variable resistor(s) in response to the measured electrical parameter.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 2 is a block diagram of a prior art architecture for coupling output current sources and current sinks to a plurality of electrodes;

FIG. 3 is a block diagram of another prior art architecture for coupling output current sources and current sinks to a plurality of electrodes;

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 4:
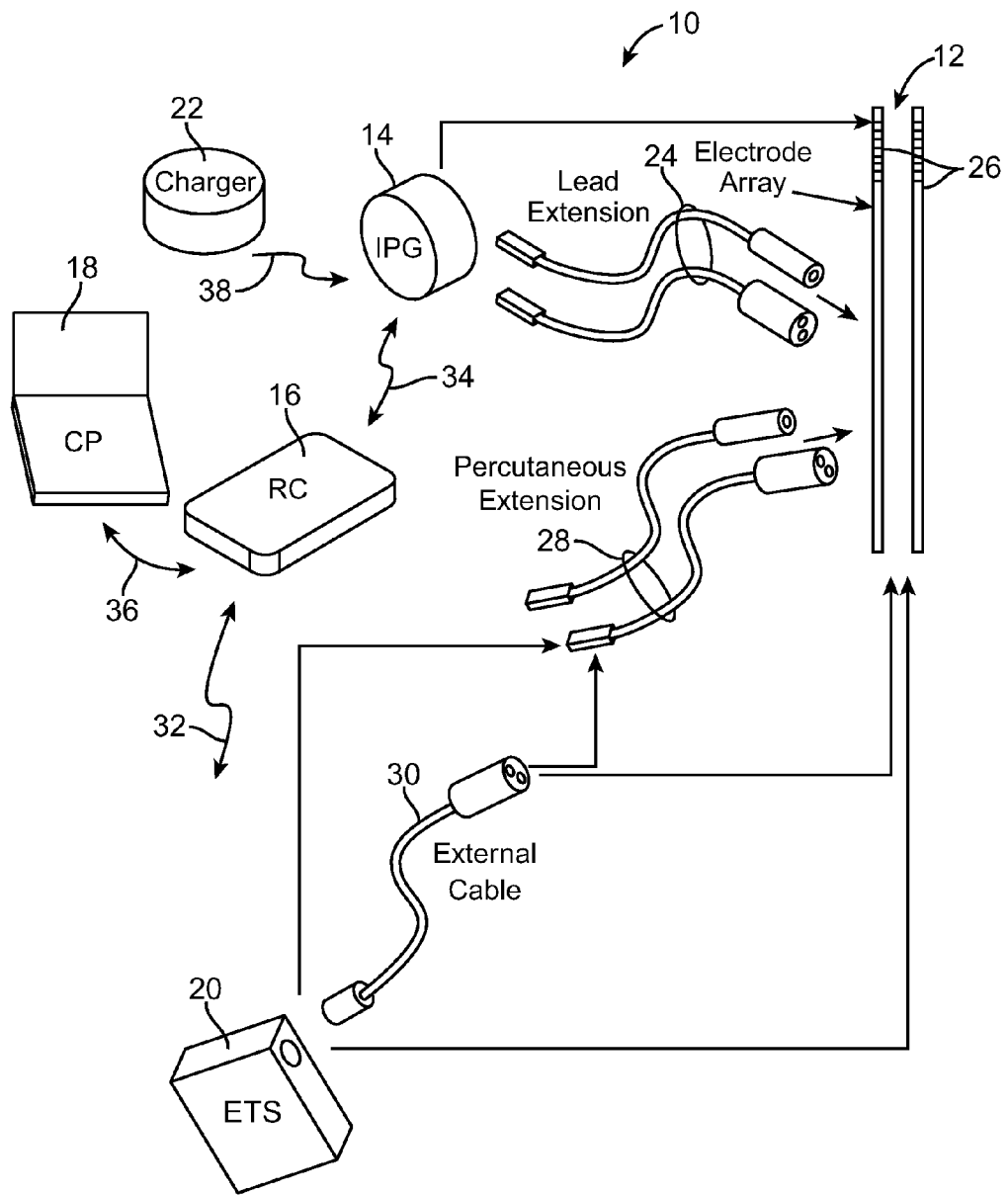
FIG. 4 is a plan view of an embodiment of a spinal cord stimulation (SCS) system arranged in accordance with the present inventions.

Turning first to FIG. 4, an exemplary SCS system 10 generally includes one or more (in this case, two) implantable stimulation leads 12, an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 5:
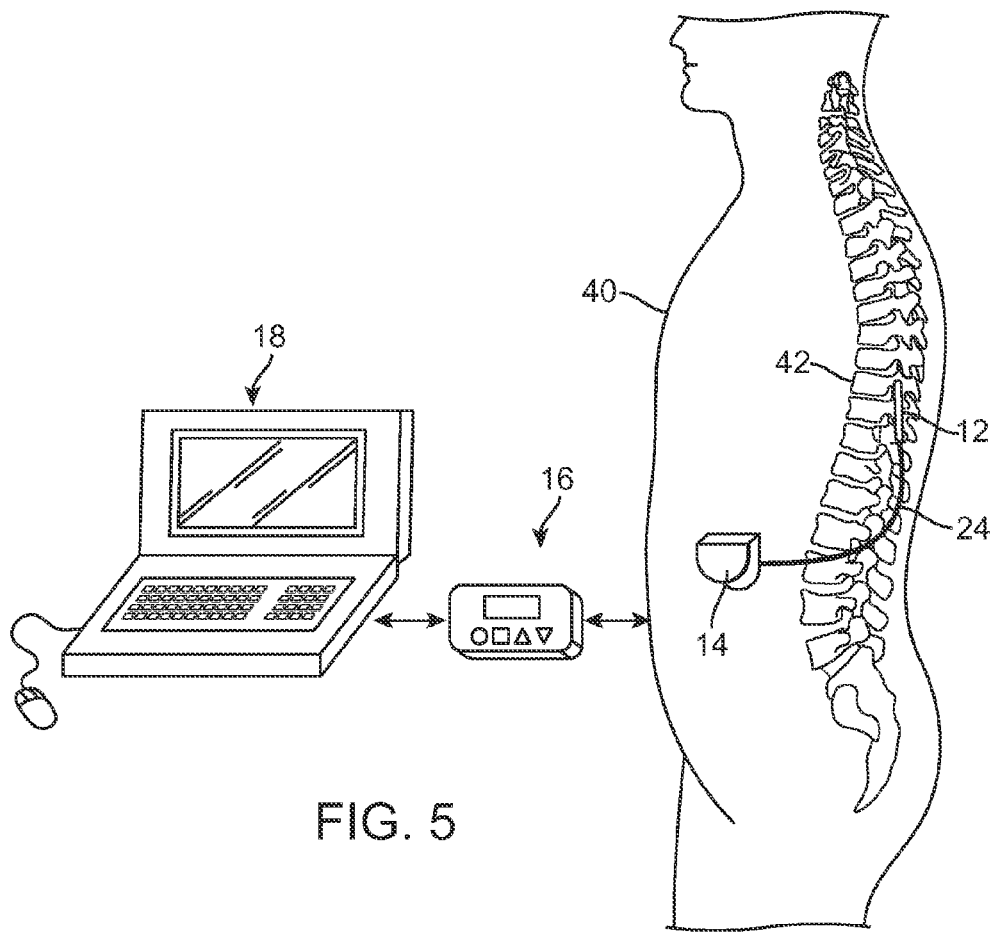
FIG. 5 is a plan view of the SCS system of FIG. 4 in use with a patient.

As shown in FIG. 5, the electrode leads 12 are implanted within the spinal column 42 of a patient 40. The preferred placement of the electrode leads 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 6:
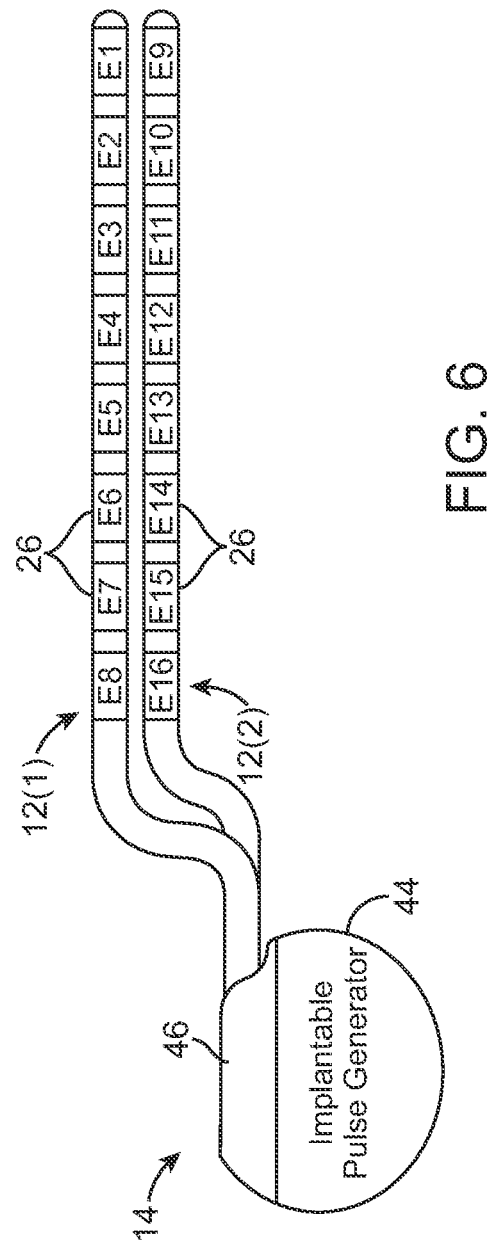
FIG. 6 is a profile view of an implantable pulse generator (IPG) used in the SCS system of FIG. 4.

Referring now to FIG. 6, the external features of the stimulation leads 12 and the IPG 14 will be briefly described. One of the stimulation leads 12(1) has eight electrodes 26 (labeled E1-E8), and the other stimulation lead 12(2) has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the stimulation leads 12(1) and 12(2) mate in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

As will be described in further detail below, the IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 1:
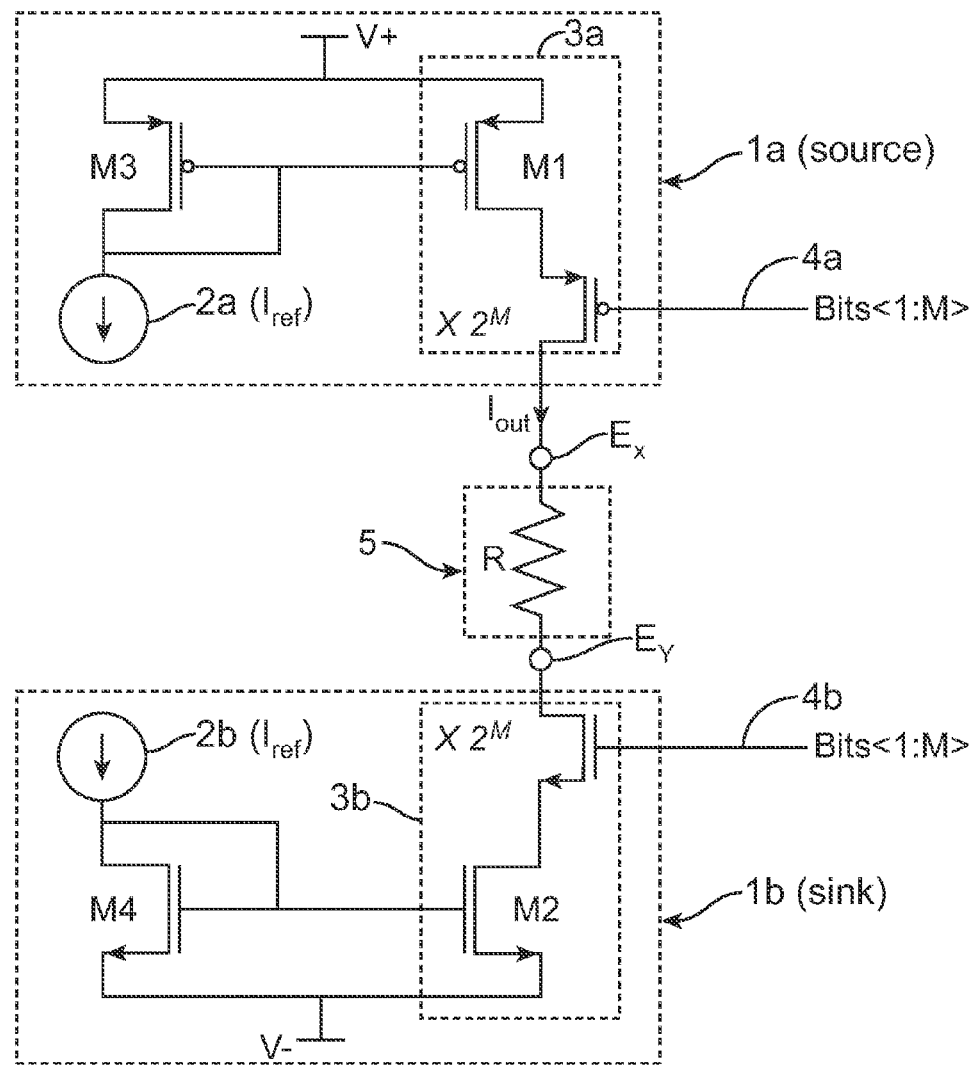
FIG. 1 is circuit diagram of a prior art embodiment of current source/current sink circuitry.
Figure 7:
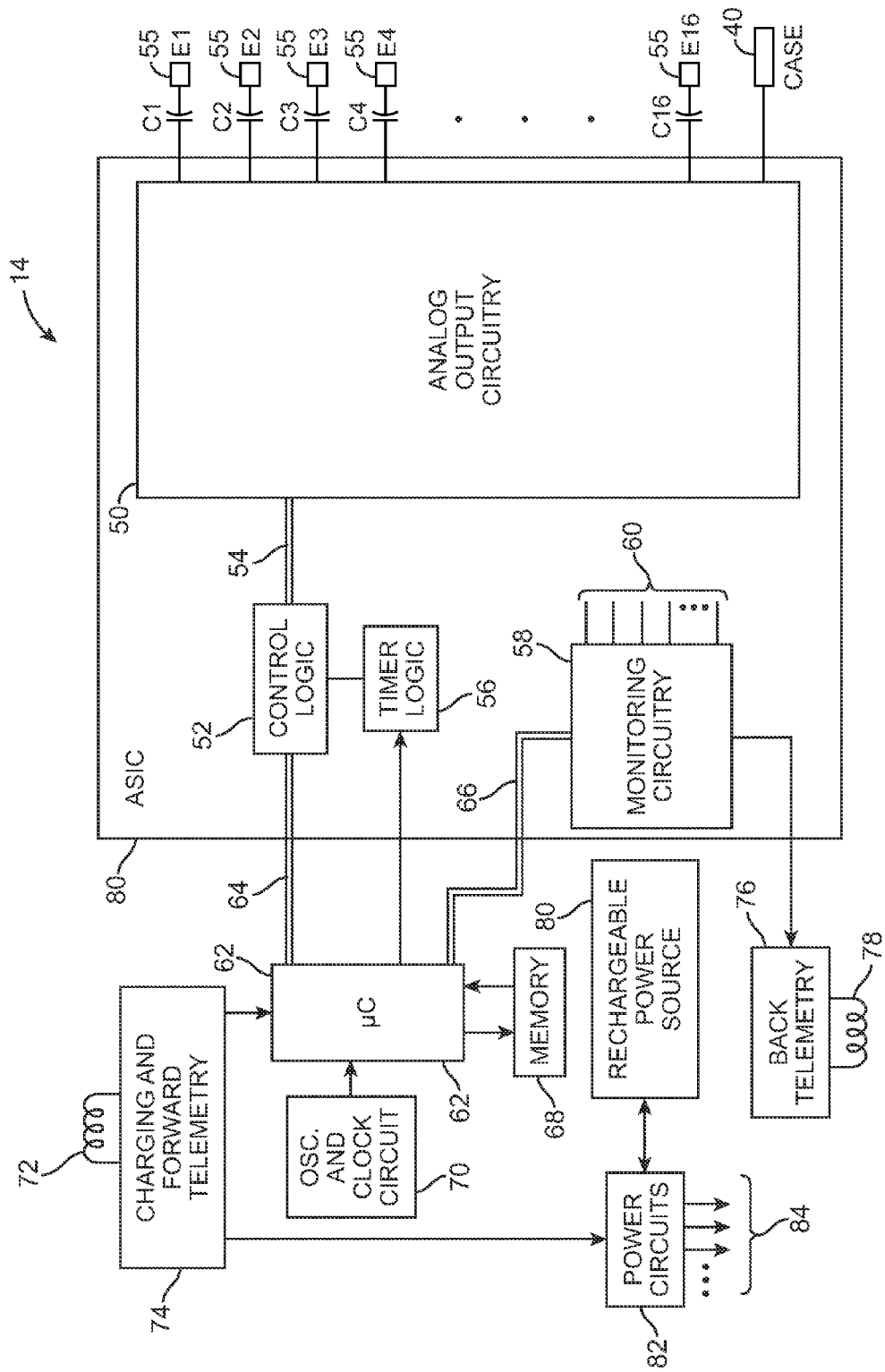
FIG. 7 is a block diagram of the internal components of the IPG of FIG. 6.

Turning next to FIG. 7, the main internal components of the IPG 14 will now be described. The IPG 14 includes analog output circuitry 50 capable of individually generating electrical stimulation pulses of specified amplitude under control of logic 52 over data bus 54. The stimulation pulses are conveyed via capacitors C1-C16 to electrical terminals 55 corresponding to the electrodes 26 (E1-E16). The duration of the electrical stimulation (i.e., the width of the stimulation pulses), is controlled by the timer logic circuitry 56. The analog output circuitry 50 may either comprise one or more independently controlled current sources and/or current sinks for providing stimulation pulses of a specified and known amperage to or from the electrodes 26, or one or more independently controlled voltage sources and/or voltage sinks for providing stimulation pulses of a specified and known voltage at the electrodes 26. The architecture of the current sources and/or current sinks may be, e.g., the same as the current source/sink architectures illustrated in FIGS. 1-3.

Any of the N electrodes may be assigned to up to k possible groups or "channels." In one embodiment, k may equal four. The channel identifies which electrodes are selected to synchronously source or sink current to create an electric field in the tissue to be stimulated. Amplitudes and polarities of electrodes on a channel may vary, e.g., as controlled by the RC 16. External programming software in the CP 18 is typically used to set stimulation parameters including electrode polarity, amplitude, pulse rate and pulse width for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a bipolar mode or multipolar mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode may be programmed to one of several discrete current levels, e.g., between 0 to 10 mA in steps of 0.1 mA. Significantly, as will be described in further detail below, variable resistances are used to adjust the magnitude of current through each electrode, thereby minimizing the number of current or voltage sources. Also, the pulse width of the current pulses is preferably adjustable in convenient increments, e.g., from 0 to 1 milliseconds (ms) in increments of 10 microseconds (µs). Similarly, the pulse rate is preferably adjustable within acceptable limits, e.g., from 0.1 to 1000 pulses per second (pps). Other programmable features can include slow start/end ramping, burst stimulation cycling (on for X time, off for Y time), interphase (i.e., the duration between first and second phases of biphasic energy), and open or closed loop sensing modes.

The operation of this analog output circuitry 50, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 58 for monitoring the status of various nodes or other points 60 throughout the IPG 14, e.g., power supply voltages, temperature, battery voltage, and the like. Notably, the electrodes 26 fit snugly within the epidural space of the spinal column, and because the tissue is conductive, electrical measurements can be taken between the electrodes 26. Thus, the monitoring circuitry 58 is configured for taking such electrical measurements (e.g., current output magnitude, electrode impedance, field potential, evoked action potentials, etc.) for performing such functions as detecting fault conditions between the electrodes 26 and the analog output circuitry 60, determining the coupling efficiency between the electrodes 26 and the tissue, facilitating lead migration detection, maintaining the desired current distribution on the active electrodes, etc.

Electrical parameter data can be measured using any one of a variety means. For example, the electrical parameter data measurements can be made on a sampled basis during a portion of the time while the electrical stimulus pulse is being applied to the tissue (e.g., if the required voltage distribution necessary to achieve the desired current distribution is to be estimated at a non-zero operating point of the stimulation), as described in U.S. Pat. No. 7,317,948, which is expressly incorporated herein by reference. Alternatively, the electrical parameter data measurements can be made independently of the electrical stimulation pulses (e.g., if the required voltage distribution necessary to achieve the desired current distribution is to be estimated at a zero operating point of the stimulation), such as described in U.S. Pat. Nos. 6,516,227 and 6,993,384, which are expressly incorporated herein by reference.

Further details discussing the measurement of electrical parameter data, such as electrode impedance, field potential, and evoked action potentials, as well as physiological parameter data, such as pressure, translucence, reflectance and pH (which can alternatively be used) are set forth in U.S. patent application Ser. No. 10/364,436, entitled "Neural Stimulation System Providing Auto Adjustment of Stimulus Output as a Function of Sensed Impedance," U.S. patent application Ser. No. 10/364,434, entitled "Neural Stimulation System Providing Auto Adjustment of Stimulus Output as a Function of Sensed Pressure Changes," and U.S. patent application Ser. No. 11/096,483, entitled "Apparatus and Methods for Detecting Migration of Neurostimulation Leads," which are expressly incorporated herein by reference.

The IPG 14 further comprises processing circuitry in the form of a microcontroller (µC) 62 that controls the control logic over data bus 64, and obtains status data from the monitoring circuitry 58 via data bus 66. The IPG 14 additionally controls the timer logic 56. The IPG 14 further comprises memory 68 and oscillator and clock circuitry 70 coupled to the microcontroller 62. The microcontroller 62, in combination with the memory 68 and oscillator and clock circuit 70, thus comprise a microprocessor system that carries out a program function in accordance with a suitable program stored in the memory 68. Alternatively, for some applications, the function provided by the microprocessor system may be carried out by a suitable state machine.

Thus, the microcontroller 62 generates the necessary control and status signals, which allow the microcontroller 62 to control the operation of the IPG 14 in accordance with a selected operating program and stimulation parameters. In controlling the operation of the IPG 14, the microcontroller 62 is able to individually generate a train of stimulus pulses at the electrodes 26 using the analog output circuitry 60, in combination with the control logic 52 and timer logic 56, thereby allowing each electrode 26 to be paired or grouped with other electrodes 26, including the monopolar case electrode. In accordance with stimulation parameters stored within the memory 68, the microcontroller 62 may control the polarity, amplitude, rate, pulse width and channel through which the current stimulus pulses are provided. The microcontroller 62 also facilitates the storage of electrical parameter data (or other parameter data) measured by the monitoring circuitry 58 within memory 68, and also provides any computational capability needed to analyze the raw electrical parameter data obtained from the monitoring circuitry 58 and compute numerical values from such raw electrical parameter data.

The IPG 14 further comprises an alternating current (AC) receiving coil 72 for receiving programming data (e.g., the operating program and/or stimulation parameters) from the RC 16 (shown in FIG. 5) in an appropriate modulated carrier signal, and charging and forward telemetry circuitry 74 for demodulating the carrier signal it receives through the AC receiving coil 72 to recover the programming data, which programming data is then stored within the memory 68, or within other memory elements (not shown) distributed throughout the IPG 14.

The IPG 14 further comprises back telemetry circuitry 76 and an alternating current (AC) transmission coil 78 for sending informational data sensed through the monitoring circuitry 58 to the RC 16. The back telemetry features of the IPG 14 also allow its status to be checked. For example, when the RC 16 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16, all programmable settings stored within the IPG 14 may be uploaded to the RC 16. Significantly, the back telemetry features allow raw or processed electrical parameter data (or other parameter data) previously stored in the memory 68 to be downloaded from the IPG 14 to the RC 16, which information can be used to track the physical activity of the patient.

The IPG 14 further comprises a rechargeable power source 80 and power circuits 82 for providing the operating power to the IPG 14. The rechargeable power source 80 may, e.g., comprise a lithium-ion or lithium-ion polymer battery. The rechargeable battery 80 provides an unregulated voltage to the power circuits 82. The power circuits 82, in turn, generate the various voltages 84, some of which are regulated and some of which are not, as needed by the various circuits located within the IPG 14. The rechargeable power source 80 is recharged using rectified AC power (or DC power converted from AC power through other means, e.g., efficient AC-to-DC converter circuits) received by the AC receiving coil 72. To recharge the power source 80, an external charger (not shown), which generates the AC magnetic field, is placed against, or otherwise adjacent, to the patient's skin over the implanted IPG 14. The AC magnetic field emitted by the external charger induces AC currents in the AC receiving coil 72. The charging and forward telemetry circuitry 74 rectifies the AC current to produce DC current, which is used to charge the power source 80. While the AC receiving coil 72 is described as being used for both wirelessly receiving communications (e.g., programming and control data) and charging energy from the external device, it should be appreciated that the AC receiving coil 72 can be arranged as a dedicated charging coil, while another coil, such as coil 78, can be used for bi-directional telemetry.

It should be noted that the diagram of FIG. 7 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As briefly discussed above, variable resistances are used to adjust the magnitude of current through each of the active electrodes 26. In particular, the analog output circuitry 50 includes variable resistors that are associated with the electrical terminals 55, and the microcontroller 62 is configured for adjusting the variable resistors, thereby modifying the magnitudes of the electrical stimulation current at the electrical terminals 55 corresponding to the active electrodes 26. The variable resistances can be adjusted, e.g., to provide effective therapy to the patient. Alternatively, the variable resistances can be adjusted to provide minimum power consumption for the given current fractionalization between the selected electrodes. Or, the variable resistances can be adjusted to compensate for changes in tissue impedance over time in order to maintain the desired current fractionalization between the selected electrodes.

Figure 8B:
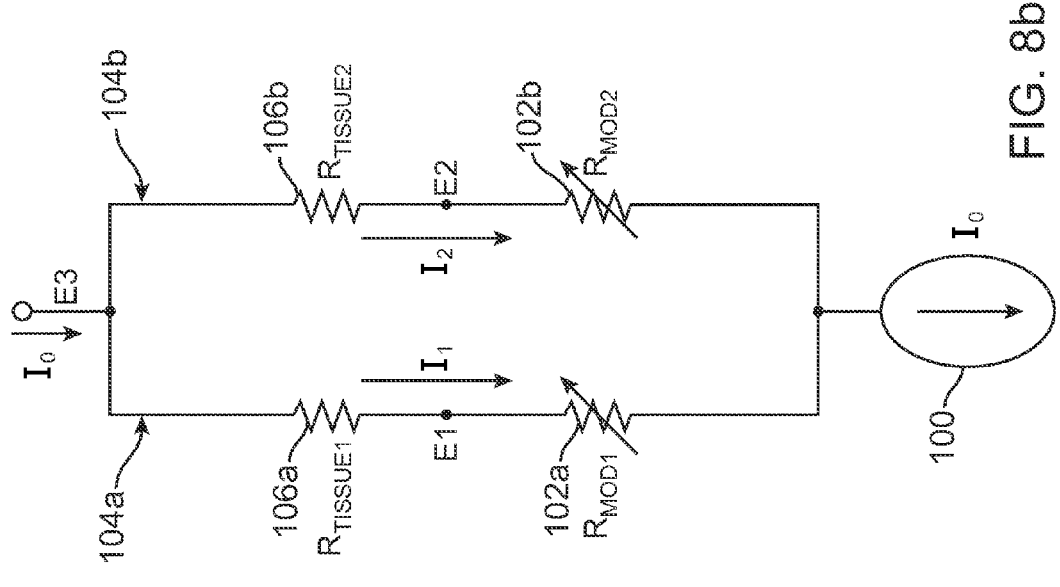
FIGS. 8a and 8b are circuit diagrams of different embodiments of electrical current steering circuitry used in the analog output circuitry of the IPG in FIG. 7.
Figure 8A:
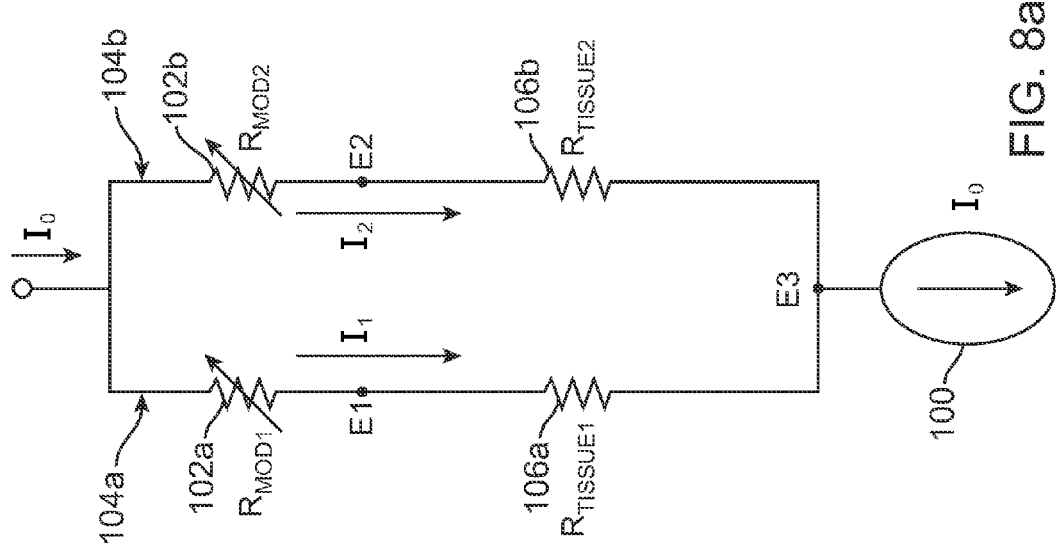

With reference to FIGS. 8a and 8b, the use of a single current source 100 and two variable resistors 102a, 102b to provide dual-electrode steering, i.e., shifting electrical current between two electrodes (in this case, electrodes E1 and E2), will now be described. As there shown, electrical stimulation current $I_0$ is generated by the current source 100 and conveyed from the two electrodes E1, E2 to a single electrode E3. In particular, the electrical stimulation current is divided into a first partial electrical current $I_1$, which is conveyed along a first electrical branch 104a consisting of the first variable resistor 102a (having a resistance value $R_{MOD1}$) and tissue 106a (having a resistance value $R_{TISSUE1}$), and a second partial electrical current $I_2$, which is conveyed along a second electrical branch 104b consisting of the second variable resistor 102b (having a resistance value $R_{MOD2}$) and tissue 106b (having a resistance value $R_{TISSUE2}$). As shown in FIG. 8a, the electrodes E1, E2 and variable resistors 102 are on the opposite side of the tissue as the current source 100. Thus, assuming that the electrodes E1, E2 are used as the stimulating electrodes, anodic electrical stimulation of the tissue is provided. As shown in FIG. 8b, the electrodes E1, E2 and variable resistors 102 are on the same side of the tissue as the current source 100. Thus, assuming that the electrodes E1, E2 are used as the stimulating electrodes, cathodic electrical stimulation of the tissue is provided.

The electrical current $I_0$ generated by the current source 100 can be adjusted to scale the absolute values of the partial electrical currents $I_1$, $I_2$ up or down. Notably, if either of the tissue resistances $R_{TISSUE1}$, $R_{TISSUE2}$ changes over time, such that the fractionalized values of the partial electrical currents $I_1$, $I_2$ change, the variable resistance values $R_{MOD1}$, $R_{MOD2}$ can be readjusted to change these fractionalized values back to their originally selected values.

The percentages (i.e., fractionalized values) of equivalent resistance within the branches 104 will determine the amount of steering according to the following equations:

$$I_1 = \frac{R_2}{R_1 + R_2} * I_0;  \quad [1]$$

$$I_2 = \frac{R_1}{R_1 + R_2} * I_0;  \quad [2]$$

$$R_1 = R_{MOD1} + R_{TISSUE1};  \quad [3]$$

and $$R_2 = R_{MOD2} + R_{TISSUE2}  \quad [4]$$

Thus, assuming that the tissue resistance values $R_{TISSUE1}$, $R_{TISSUE2}$ are constant, it can be appreciated that the fractionalized values of the partial electrical currents $I_1$, $I_2$ flowing through the respective branches 104, and thus, at the two electrodes E1, E2, can be determined from the variable resistance values $R_{MOD1}$, $R_{MOD2}$. It follows that the values to which the variable resistance values $R_{MOD1}$, $R_{MOD2}$ should be adjusted to obtain the desired fractionalized values for the partial electrical currents $I_1$, $I_2$ can be computed from equations [1]-[4] in a conventional manner.

For example, constraining the equations [1]-[4], such that only one of the variable resistance values $R_{MOD1}$, $R_{MOD2}$ has a finite value at any given time (i.e., resistance is only added to one of the current branches 106), these equations can be rearranged as follows to solve for the variable resistance values:

$$R_{MOD1} = \begin{cases} 0, & \text{if } I1 \geq \frac{R_{TISSUE2}}{R_{TISSUE1} + R_{TISSUE2}} \\ R_{TISSUE2}(1 - I1) - \frac{I1 * R_{TISSUE1}}{I1}, & \text{otherwise} \end{cases}  \quad [5]$$

$$R_{MOD2} = \begin{cases} 0, & \text{if } I1 \leq \frac{R_{TISSUE2}}{R_{TISSUE1} + R_{TISSUE2}} \\ I1 * R_{TISSUE1} + \frac{R_{TISSUE2}(I1 - 1)}{1 - I1}, & \text{otherwise} \end{cases}  \quad [6]$$

Notably, while equations [5] and [6] provide a unique solution for the ratio of the variable resistance values $R_{MOD1}$, $R_{MOD2}$, equations [5] and [6] provide an indeterminate solution for the absolute resistance values $R_{MOD1}$, $R_{MOD2}$. The absolute resistance values $R_{MOD1}$, $R_{MOD2}$ should be scaled up or down based on the absolute tissue resistance values $R_{TISSUE1}$, $R_{TISSUE2}$. That is, the variable resistance values $R_{MOD1}$, $R_{MOD2}$ should be increased as tissue resistance values $R_{TISSUE1}$, $R_{TISSUE2}$ increase, and the variable resistance values $R_{MOD1}$, $R_{MOD2}$ should be decreased as tissue resistance values $R_{TISSUE1}$, $R_{TISSUE2}$ decrease. All changes of $R_{MOD1}$, $R_{MOD2}$ in response to changes in $R_{TISSUE1}$, $R_{TISSUE2}$ should be such that the desired ratio of current flow between I1 and I2 is maintained as programmed. In this manner, the design of the variable resistors 102 can be customized to the anticipated tissue resistance values $R_{TISSUE1}$, $R_{TISSUE2}$, thereby providing a more efficient design. For example, the minimum amount of additional resistance $R_{MODX}$ is added on all electrodes providing the maximum power transfer efficiency to the tissue.

Figure 9A:
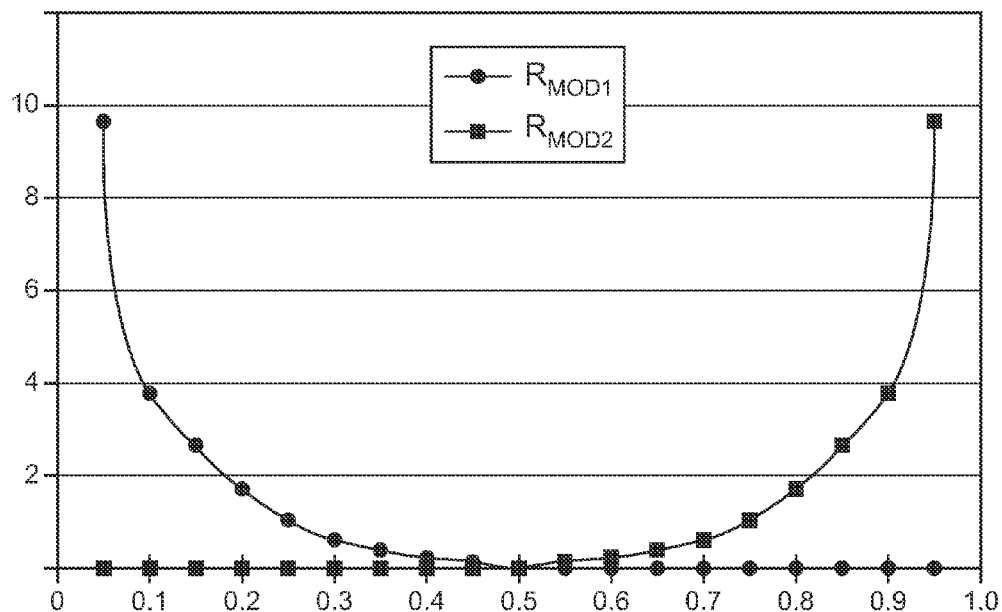
FIGS. 9a-9f are plots of the values used in the variable resistors of FIGS. 8a and 8b versus the fractionalized values of one of the electrical currents.

For example, given a normalized resistance of 375 ohms, and assuming a normalized tissue value $R_{TISSUE1}$=0.53 (200 ohms), and a normalized tissue value $R_{TISSUE2}$=0.53 (200 ohms), the normalized variable resistance values $R_{MOD1}$, $R_{MOD2}$ may be computed using equations [5] and [6] and plotted against a desired fractionalized current value I1, as shown in FIG. 9a. As there shown, to achieve fractionalized current values I1 in the range of 5%-95%, each of the normalized variable resistance values $R_{MOD1}$, $R_{MOD2}$ must be adjustable within the range of 0-9.5.

Figure 9B:
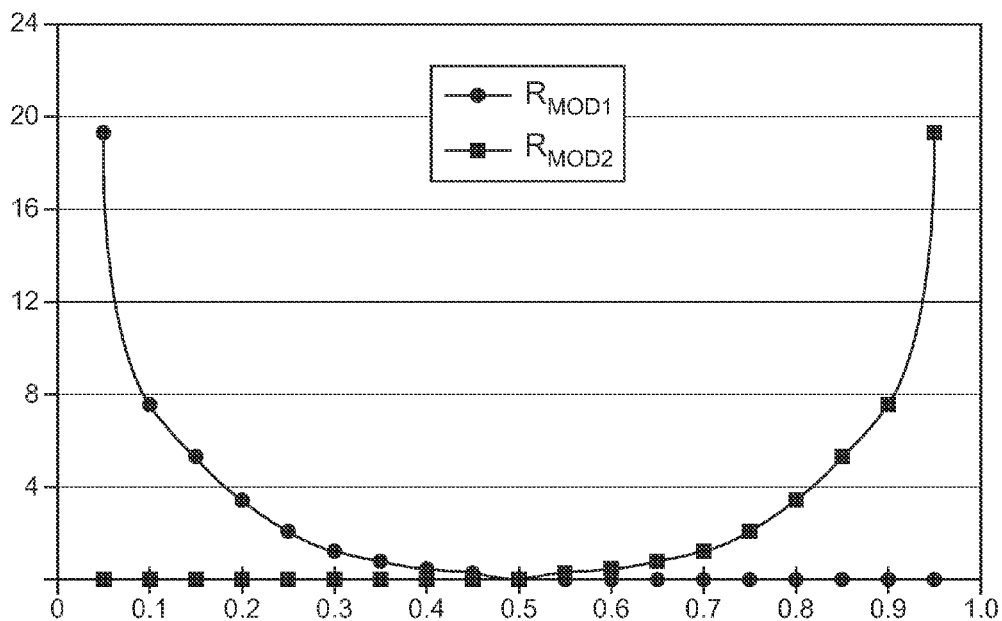

As another example, given a normalized resistance of 375 ohms, and assuming a normalized tissue value $R_{TISSUE1}$=1.07 (400 ohms), and a normalized tissue value $R_{TISSUE2}$=1.07 (400 ohms), the normalized variable resistance values $R_{MOD1}$, $R_{MOD2}$ may be computed using equations [5] and [6] and plotted against a desired fractionalized current value I1, as shown in FIG. 9b. As there shown, to achieve fractionalized current values I1 in the range of 5%-95%, each of the normalized variable resistance values $R_{MOD1}$, $R_{MOD2}$ must be adjustable within the range of 0-19.

Figure 9C:
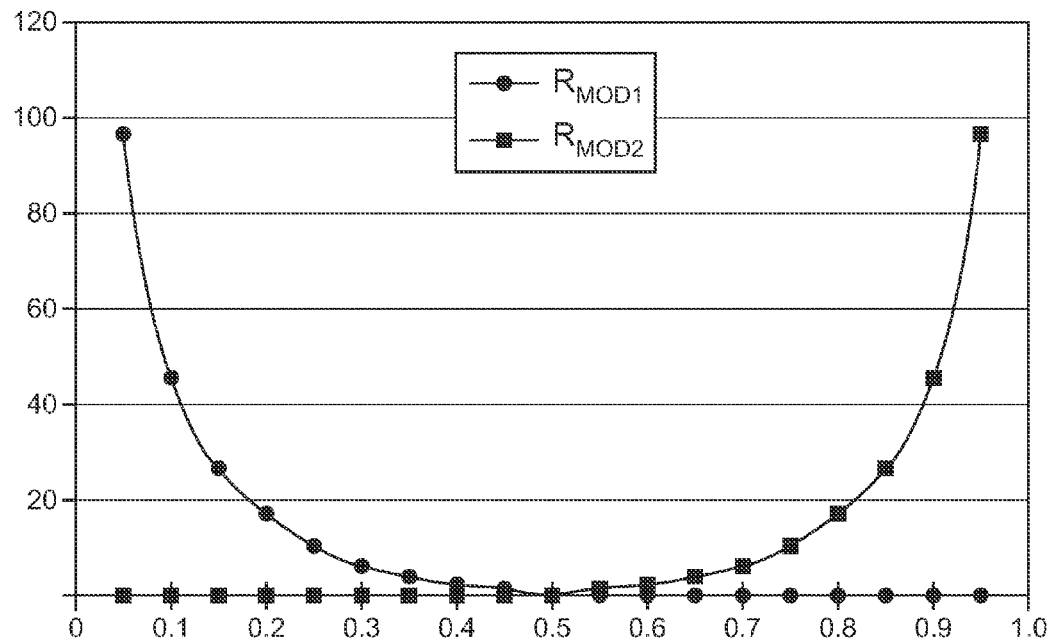

As still another example, given a normalized resistance of 375 ohms, and assuming a normalized tissue value $R_{TISSUE1}$=5.3 (2000 ohms), and a normalized tissue value $R_{TISSUE2}$=5.3 (2000 ohms), the normalized variable resistance values $R_{MOD1}$, $R_{MOD2}$ may be computed using equations [5] and [6] and plotted against a desired fractionalized current value I1, as shown in FIG. 9c. As there shown, to achieve fractionalized current values I1 in the range of 5%-95%, each of the normalized variable resistance values $R_{MOD1}$, $R_{MOD2}$ must be adjustable within the range of 0-95.

Figure 9D:
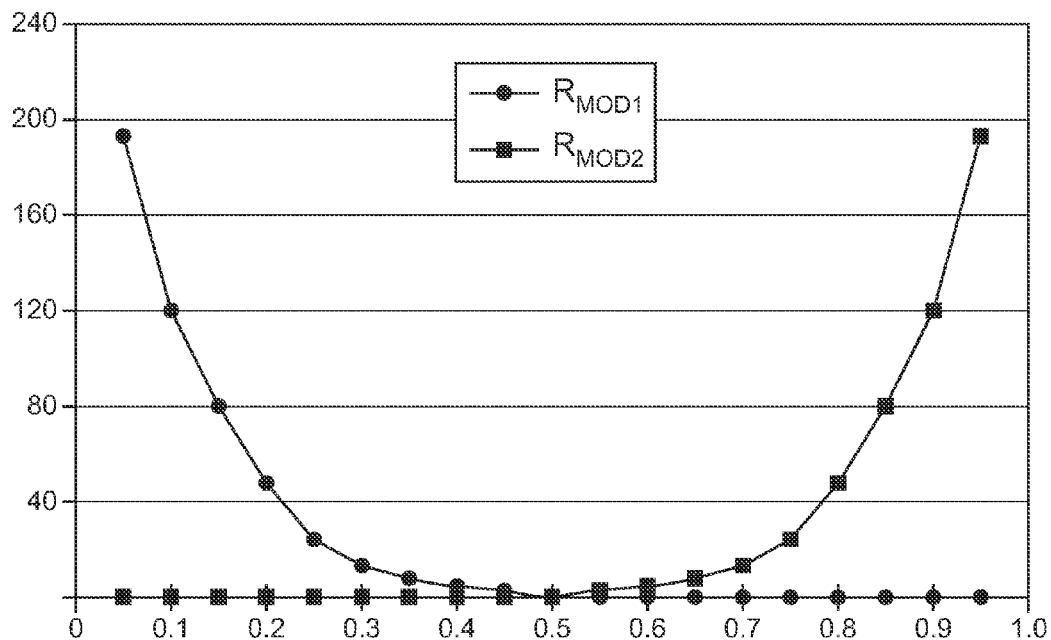

As yet another example, given a normalized resistance of 375 ohms, and assuming a normalized tissue value $R_{TISSUE1}$=10.7 (4000 ohms), and a normalized tissue value $R_{TISSUE2}$=10.7 (4000 ohms), the normalized variable resistance values $R_{MOD1}$, $R_{MOD2}$ may be computed using equations [5] and [6] and plotted against a desired fractionalized current value I1, as shown in FIG. 9d. As there shown, to achieve fractionalized current values I1 in the range of 5%-95%, each of the normalized variable resistance values $R_{MOD1}$, $R_{MOD2}$ must be adjustable within the range of 0-195.

Notably, due to the equality between the normalized tissue values $R_{TISSUE1}$, $R_{TISSUE2}$ in the examples illustrated in FIGS. 9a-9d, the adjustments of the respective variable resistance values $R_{MOD1}$, $R_{MOD2}$ are symmetric across the fractionalized current range of 5%-95%, and the fractionalized current ranges across which the variable resistance values $R_{MOD1}$, $R_{MOD2}$ are adjusted are of equal size, with the variable resistance value $R_{MOD1}$ being adjusted in the fractionalized current range of 5%-50%, and the variable resistance value $R_{MOD2}$ being adjusted in the fractionalized current range of 50%-95%. If the normalized tissue values $R_{TISSUE1}$, $R_{TISSUE2}$ are unequal, however, the adjustments of the respective variable resistance values $R_{MOD1}$, $R_{MOD2}$ will be asymmetric across the fractionalized current range of 5%-95%, and the fractionalized current ranges across which the variable resistance values $R_{MOD1}$, $R_{MOD2}$ are adjusted will be of unequal size.

Figure 9E:
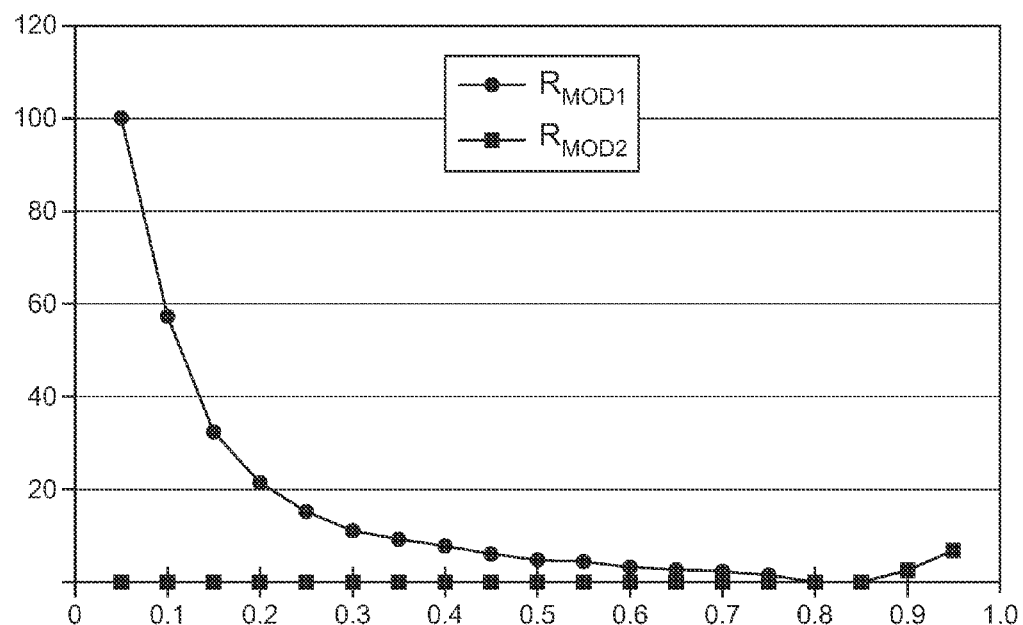

For example, given a normalized resistance of 375 ohms, and assuming a normalized tissue value $R_{TISSUE1}$=0.53 (200 ohms), and a normalized tissue value $R_{TISSUE2}$=5.3 (2000 ohms), the normalized variable resistance values $R_{MOD1}$, $R_{MOD2}$ may be computed using equations [5] and [6] and plotted against a desired fractionalized current value I1, as shown in FIG. 9e. As there shown, to achieve fractionalized current values I1 in the range of 5%-95%, the normalized variable resistance values $R_{MOD1}$ must be adjustable within the range of 0-100 along the fractionalized current range of 5%-87%, and the normalized variable resistance value $R_{MOD2}$ must be adjustable within the range of 0-4.8 along the fractionalized current range of 87%-95%.

As another example, given a normalized resistance of 375 ohms, and assuming a normalized tissue value $R_{TISSUE1}$=0.53 (200 ohms), and a normalized tissue value $R_{TISSUE2}$=10.7

Figure 9F:
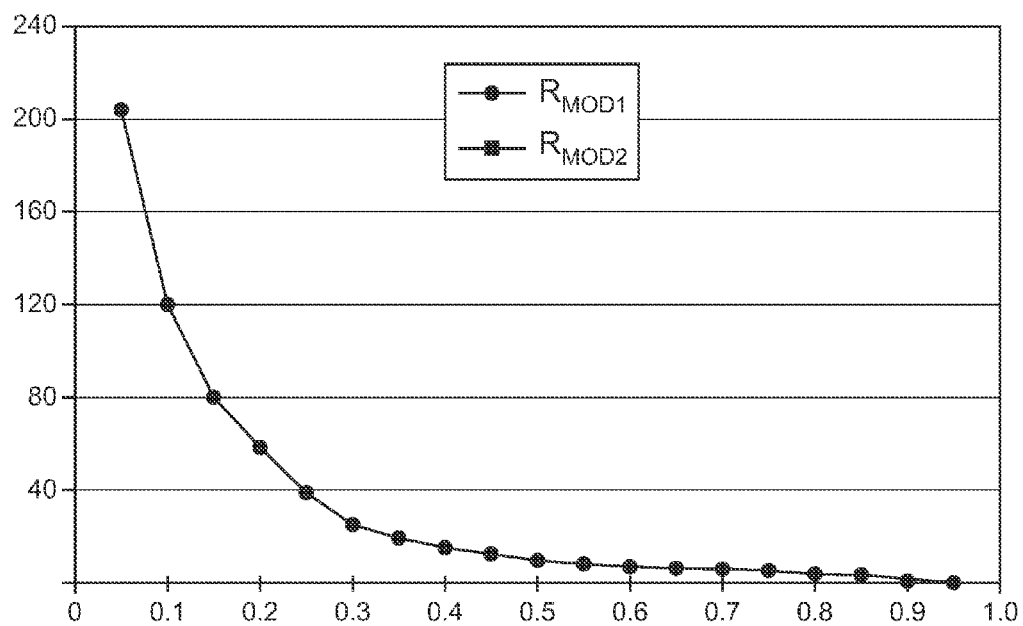

(4000 ohms), the normalized variable resistance values $R_{MOD1}$, $R_{MOD2}$ may be computed using equations [5] and [6] and plotted against a desired fractionalized current value I1, as shown in FIG. 9f. As there shown, to achieve fractionalized current values I1 of 5%-95%, the normalized variable resistance values $R_{MOD1}$ must be adjustable within the range of 0-205 along the fractionalized current range of 5%-95%. The inequality between the normalized tissue values $R_{TISSUE1}$, $R_{TISSUE2}$ is so great, that the variable resistance value $R_{MOD2}$ may be zero, essentially obviating the need for having the variable resistance value $R_{MOD2}$.

The simplicity of using a single current source for steering current between two electrodes is quite advantageous, especially when low-resolution current steering is to be achieved. Although only one current source is illustrated in FIGS. 8a and 8b, multiple current sources can be provided in the analog output circuitry 50, with at least one of the current sources providing steering capability to multiple electrodes.

It should be noted that current steering between two electrodes can be accomplished with the use of only one variable resistor. In this case, the variable resistor is incorporated into the branch anticipated to have the least amount of current flowing through it. In a dual-steering arrangement, assuming that the tissue resistance values $R_{TISSUE1}$, $R_{TISSUE2}$ are equal to each other and that each of the variable resistance values $R_{MOD1}$, $R_{MOD2}$ can be varied between 0 and infinity, the fractionalized value of the partial electrical current ($I_1$ or $I_2$) flowing in the branch having the variable resistor theoretically has a fractionalized current range of 0-50%, and the fractionalized value of the partial electrical current ($I_2$ or $I_1$) flowing in the branch without the variable resistor theoretically has a fractionalized current range of 50-100%.

Figure 10:
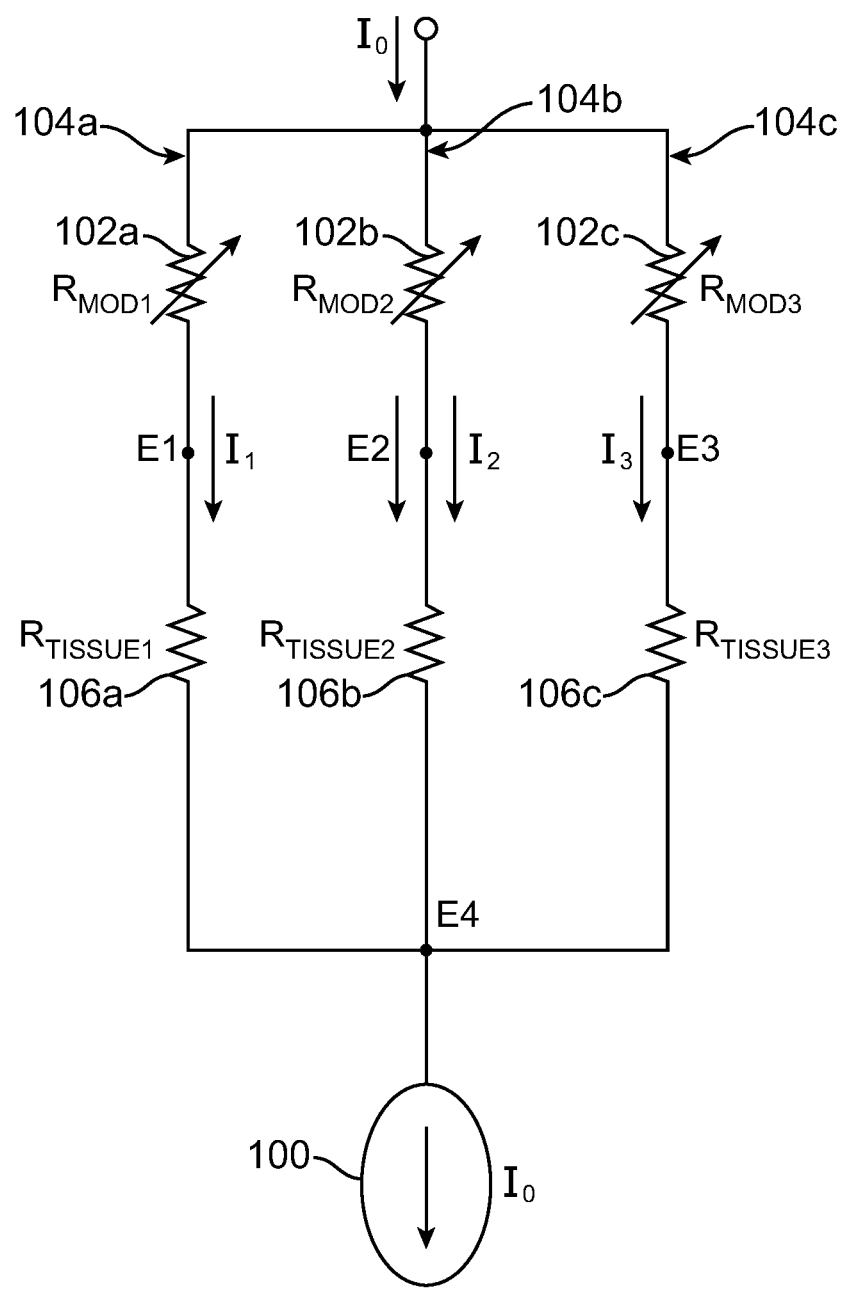
FIG. 10 is a circuit diagram of another embodiment of electrical current steering circuitry used in the analog output circuitry of the IPG in FIG. 7.

It should also be noted that a single current source can be used to steer current between more than two electrodes. For example, with reference to FIG. 10, the current source 100 and three variable resistors 102a, 102b, 102c are used to provide tri-electrode steering, i.e., shifting electrical current between three electrodes (in this case, electrodes E1, E2, E3). As there shown, electrical stimulation current $I_0$ is generated by the current source 100 and conveyed from the three electrodes E1, E2, E3 to a single electrode E4.

In particular, the electrical stimulation current $I_0$ is divided into a first partial electrical current $I_1$, which is conveyed along a first electrical branch 104a consisting of the first variable resistor 102a (having a resistance value $R_{MOD1}$) and tissue 106a (having a resistance value $R_{TISSUE1}$), a second partial electrical current $I_2$, which is conveyed along a second electrical branch 104b consisting of the second variable resistor 102b (having a resistance value $R_{MOD2}$) and tissue 106b (having a resistance value $R_{TISSUE2}$), and a third electrical branch 104c consisting of the third variable resistor 102c (having a resistance value $R_{MOD3}$) and tissue 106c (having a resistance value $R_{TISSUE3}$).

The fractionalized values of the equivalent resistances within the branches 104 will determine the amount of steering according to the following equations:

$$I_1 = \frac{R_1 R_2 R_3}{R_1(R_1 R_2 + R_2 R_3 + R_2 R_3)} * I_0; \quad [7]$$

$$I_2 = \frac{R_1 R_2 R_3}{R_2(R_1 R_2 + R_2 R_3 + R_2 R_3)} * I_0; \quad [8]$$

and $$I_3 = \frac{R_1 R_2 R_3}{R_3(R_1 R_2 + R_2 R_3 + R_2 R_3)} * I_0; \quad [9]$$

$$R_1 = R_{MOD1} + R_{TISSUE1}; \quad [10]$$

$$R_2 = R_{MOD2} + R_{TISSUE2}; \quad [11]$$

and $$R_3 = R_{MOD3} + R_{TISSUE3} \quad [12]$$

Thus, assuming that the tissue resistance values $R_{TISSUE1}$, $R_{TISSUE2}$, $R_{TISSUE3}$ are constant, it can be appreciated that the fractionalized values of the partial electrical currents $I_1$, $I_2$, $I_3$ flowing through the respective branches 104, and thus, at the three electrodes E1, E2, E3 can be determined from the variable resistance values $R_{MOD1}$, $R_{MOD2}$, $R_{MOD3}$. It follows that the values to which the variable resistance values $R_{MOD1}$, $R_{MOD2}$, $R_{MOD3}$ should be adjusted to obtain the fractionalized values of the desired partial electrical currents $I_1$, $I_2$, $I_3$ can be computed from equations [7]-[12] in a conventional manner. As in the previous case, the electrical current $I_0$ generated by the current source 100 can be adjusted to scale the absolute values of the partial electrical currents $I_1$, $I_2$, $I_3$ up or down, and if either of the tissue resistances $R_{TISSUE1}$, $R_{TISSUE2}$, $R_{TISSUE3}$ changes over time, such that the fractionalized values of the partial electrical currents $I_1$, $I_2$, $I_3$ change, the variable resistance values $R_{MOD1}$, $R_{MOD2}$, $R_{MOD3}$ can be readjusted to change the fractionalized values of the partial electrical currents $I_1$, $I_2$, $I_3$ back to their originally selected values.

Figure 11:
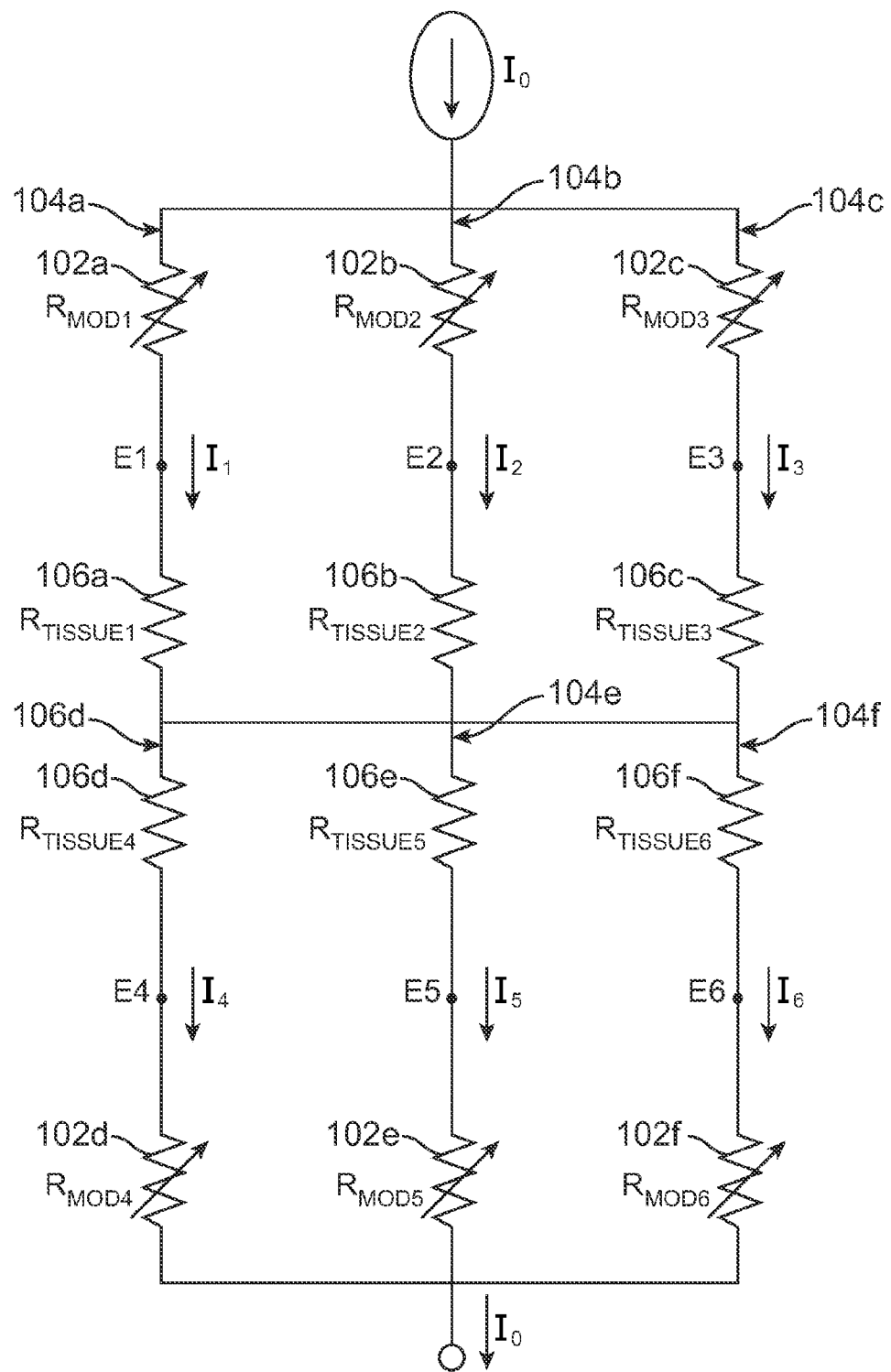
FIG. 11 is a circuit diagram of still another embodiment of electrical current steering circuitry used in the analog output circuitry of the IPG in FIG. 7.

It should also be noted that a current source and variable resistors can be used to steer both anodic current between a group of electrodes, and cathodic current between another group of electrodes. For example, with reference to FIG. 11, a current source 100a and a group of variable resistors 102a-102c are used to provide multi-electrode anodic steering between anodic electrodes E1-E3, and the current source 100a and a group of variable resistors 102d-102f are used to provide multi-electrode cathodic steering between cathodic electrodes E4-E6. As there shown, electrical stimulation current $I_0$ is generated by the current source 100a and is conveyed from the anodic electrodes E1-E3 to cathodic electrodes E4-E6. An optional addition current source 100c can be provided to sink the stimulation current $I_0$ from the cathodic electrodes E4-E6. It should be appreciated that, although anodic current steering is shown as being provided for three electrodes, and cathodic current steering is shown as being provided with three electrodes, the anodic current steering and cathodic current steering can each be provided between any plural number of electrodes (including two, four, etc.).

The electrical stimulation current $I_0$ is divided into partial electrical current $I_1$, which is conveyed along a first electrical branch 104a consisting of the first variable resistor 102a (having a resistance value $R_{MOD1}$) and tissue 106a (having a resistance value $R_{TISSUE1}$), a second partial electrical current $I_2$, which is conveyed along a second electrical branch 104b consisting of the second variable resistor 102b (having a resistance value $R_{MOD2}$) and tissue 106b (having a resistance value $R_{TISSUE2}$), and a third electrical branch 104c consisting of the third variable resistor 102c (having a resistance value $R_{MOD3}$) and tissue 106c (having a resistance value $R_{TISSUE3}$).

The electrical stimulation current $I_0$ is divided into partial electrical current $I_4$, which is conveyed along a fourth electrical branch 104d consisting of the fourth variable resistor 102d (having a resistance value $R_{MOD4}$) and tissue 106d (having a resistance value $R_{TISSUE4}$), a fifth partial electrical current $I_5$, which is conveyed along a fifth electrical branch 104e consisting of the fifth variable resistor 102e (having a resistance value $R_{MOD5}$) and tissue 106e (having a resistance value $R_{TISSUE5}$), and a sixth electrical branch 104f consisting of the sixth variable resistor 102f (having a resistance value $R_{MOD6}$) and tissue 106f (having a resistance value $R_{TISSUE6}$).

The resistance values $R_{MOD}$ of the variable resistors 102 may be set to their correct values by measuring the partial electrical currents through the respective electrodes 106 and adjusting the resistance values $R_{MOD}$ until the measured partial electrical currents equal the desired partial electrical currents through the respective electrodes 106.

It should be appreciated that, although the embodiments illustrated in FIGS. 8a-8b, 10, and 11 use a current source, alternative embodiments may utilize voltage sources, as briefly discussed above. In this case, the current generated by the voltage source may be maintained at a constant defined current as the variable resistors 102 are adjusted by computing and varying the voltage output by the voltage source based on the total resistances between the active electrodes. One technique for maintaining a constant current using a voltage source is described in U.S. Provisional Patent Application Ser. No. 61/083,491, entitled "System and Method for Maintaining a Distribution of Currents in an Electrode Array Using Independent Voltage Sources," which is expressly incorporated herein by reference.

The variable resistors 102 used in the embodiments illustrated in FIGS. 8a-8b, 10, and 11 may take the form of any resistor whose value can be actively varied via a control signal, but in the preferred embodiment, the variable resistors take the form of programmable on-chip resistors to minimize the space required by the variable resistors. Each variable resistor preferably can be adjusted to a finite value (i.e., a value somewhere between a virtual short circuit (resistance approximately 0) and a virtual open circuit (a resistance of infinity). In other words, a finite variable resistor is not a simple switch that turns on and off.

Figure 12A:
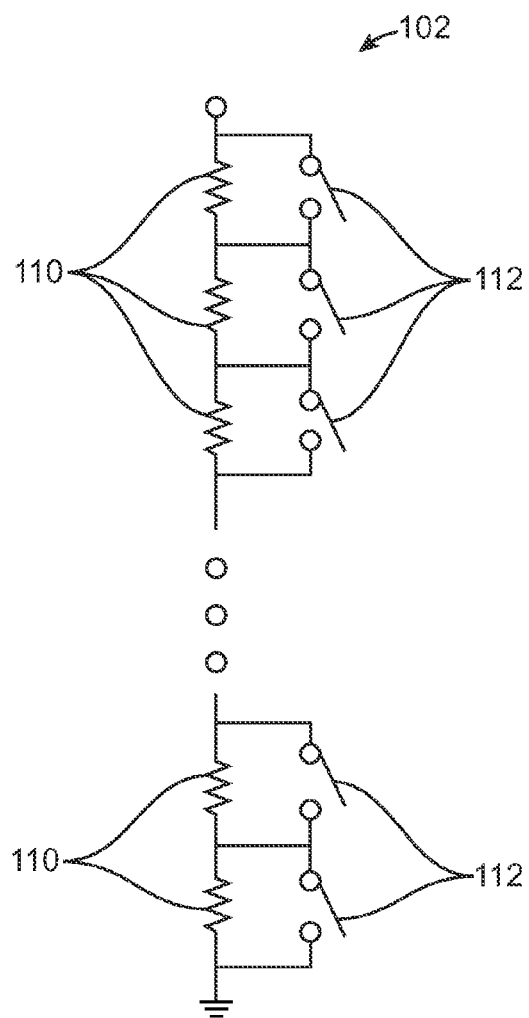
FIGS. 12a and 12b are circuit diagrams of different embodiments of a variable resistor for use in the IPG in FIG. 7.
Figure 12B:
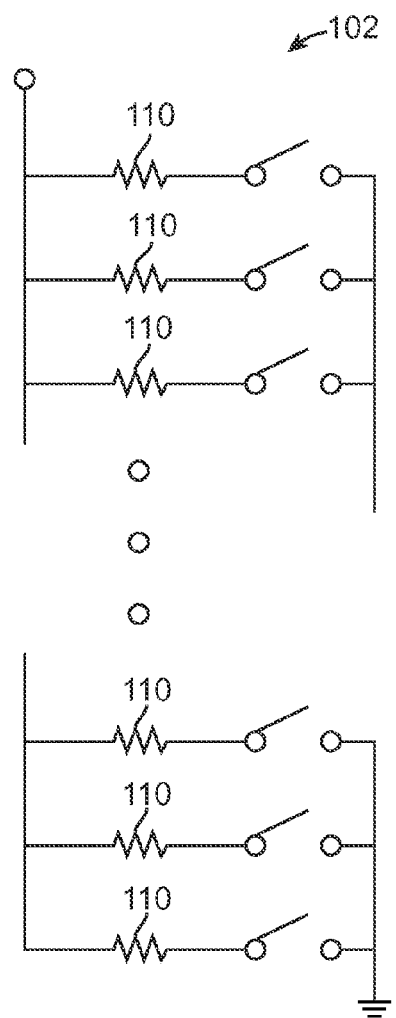

In one embodiment, each variable resistor 102 comprises a multitude of series-connected resistive elements 110 that can be selected through shunt switches 112, as illustrated in FIG. 12a. In this case, the resistance value of the variable resistor increases as the number of open shunt switches 112 increases, and decreases as the number of closed shunt switches 112 increases. In another embodiment, each variable resistor comprises a multitude of parallel-connected resistive elements 110 that can be selected through switches 112 connected in series with the respective resistive elements 110, as illustrated in FIG. 12b. In this case, the resistance value of the variable resistor increases as the number of open switches 112 increases, and decreases as the number of closed switches 112 increases. The switches in either of the embodiments illustrated in FIGS. 12a and 12b may be adequately controlled to adjust the actual value of the variable resistor to the target resistance value. In other embodiments, some of the resistive elements 110 may be connected in series, and other resistive elements 110 may be connected in parallel.

Control of the partial electrical currents at the activated electrodes may be accomplished in a variety of manners and performed by either the IPG 14 or an external control device (such as, e.g., the RC 16 and/or CP 18).

In one embodiment, the external control device wirelessly transmits a command to the IPG 14 to measure the tissue resistances within the current branches associated with the activated electrodes 26. The forward telemetry circuitry 74 receives the command, and the monitoring circuitry 58, under control by the microcontroller 62, measures the tissue resistances. The back telemetry circuitry 76, under control by the microcontroller 62, then wirelessly transmits the measured tissue resistances back to the external control device. Based on the measured tissue resistances, the external control device computes the values of the variable resistances needed to obtain the desired fractionalized currents at the activated electrodes 26 (e.g., 80% in electrode E1 and 20% in electrode E2); for example, by computing the variable resistances from equations [1]-[6] or equations [7]-[12]. The external control device then wirelessly transmits a control signal containing the desired variable resistances to the IPG 14. The forward telemetry circuitry 74, under control by the microcontroller 62, receives the control signal, and the analog output circuitry 50, under control of the microcontroller 62, adjusts the variable resistors 102 to the desired resistance values.

In another embodiment, the external control device wirelessly transmits a control signal containing the desired fractionalized currents at the activated electrodes 26 to the IPG 14. The forward telemetry circuitry 74, under control by the microcontroller 62, receives the control signal, and the microcontroller 62, based on measured tissue resistances (performed by the monitoring circuitry 58 either prior to or after receipt of the control signal), computes the values of the variable resistances needed to obtain the desired fractionalized currents at the activated electrodes 26; for example, by computing the variable resistances from equations [1]-[6] or equations [7]-[12]. The analog output circuitry 50, under control of the microcontroller 62, then adjusts the variable resistors 102 to the desired resistance values. Alternatively, rather than computing the values of the variable resistances, the monitoring circuitry 58 may measure the electrical current at the activated electrodes 26, and the analog output circuitry 50, under control of the microcontroller 62, can adjust the variable resistors 102 until the measured electrical currents at the activated electrodes 26 match the desired fractionalized values of the electrical currents. In either case, the microcontroller 62 may either adjust the variable resistors 102 to achieve the desired electrical current distribution only in response to a command received by the external control device, or may periodically monitor the electrical currents at the activated electrodes 26 and adjust the variable resistors 102, if needed, to maintain the desired electrical current distribution at the activated electrodes 102 in a closed loop fashion.

It should be noted that the technique of steering electrical stimulation current between electrodes using variable resistors can be used in the ETS 20. In this case, electrical current, under control of the ETS and external control device, can be steering between the electrodes to determining one or more sets of stimulation parameters that provide effective therapy to the patient. The current distribution can either be measured in the ETS 20 or estimated based on the effective variable resistances. Once the stimulation parameter sets, including the effective current distributions, are determined, they can be programmed into the IPG. This technique may be particularly advantageous when the IPG has no variable resistors and has minimal or no computer power, which may otherwise be needed to perform the techniques described herein.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient implanted with a plurality of electrodes, the method comprising:
conveying electrical stimulation current from at least two of the electrodes to at least one of the electrodes along at least two electrical paths through tissue of the patient; and
shifting the electrical stimulation current between the at least two electrical paths by actively adjusting one or more finite resistances respectively associated with one or more of the at least two electrical paths.

2. The method of claim 1, wherein the at least one of the electrodes is a plurality of electrodes.

3. The method of claim 1, wherein the electrical stimulation current is generated by a single current source.

4. The method of claim 3, further comprising adjusting the magnitude of the electrical stimulation current generated by the single current source.

5. The method of claim 1, wherein the electrical stimulation current is cathodic.

6. The method of claim 1, wherein the electrical stimulation current is anodic.

7. The method of claim 1, wherein the one or more finite resistances includes at least two finite resistances respectively associated with the at least two electrical paths.

8. The method of claim 1, further comprising transcutaneously transmitting a control signal, wherein the at least one finite resistance is actively adjusted in response to the control signal.

9. The method of claim 8, wherein the control signal designates at least two magnitude values for the electrical stimulation current respectively along the at least two electrical paths, and wherein the one or more finite resistances are adjusted to set the electrical stimulation current in the at least two electrical paths respectively to the at least two magnitude values.

10. The method of claim 9, wherein the at least two magnitude values are fractionalized.

11. The method of claim 8, wherein the control signal designates one or more resistance values, and wherein the one or more finite resistances is respectively adjusted to the one or more resistance values.

12. The method of claim 1, further comprising measuring one or more electrical parameters respectively associated with one or more of the at least two electrical paths, wherein the one or more finite resistances are adjusted in response to the one or more measured electrical parameters.

13. The method of claim 12, wherein the one or more electrical parameters comprises one or more magnitudes of current in the one or more electrical paths.

14. The method of claim 12, wherein the one or more electrical parameters comprises one or more impedances in the one or more electrical paths.

15. The method of claim 1, further comprising:
determining at least one stimulator parameter in accordance with which the conveyed electrical stimulation current provides effective therapy to the patient; and
programming an implanted neurostimulator with the at least one stimulation parameter.

16. The method of claim 1, further comprising implanting the plurality of electrodes within the patient.

17. A neurostimulation system, comprising:
a plurality of electrical terminals configured for being respectively coupled to a plurality of electrodes;
analog output circuitry configured for conveying electrical stimulation current from at least two of the electrical terminals to at least another of the electrical terminals through tissue, wherein the analog output circuitry includes one or more variable resistors respectively coupled to one or more of the electrical terminals; and
control circuitry configured for adjusting the one or more variable resistors, thereby modifying the magnitudes of the electrical stimulation current at the at least two electrical terminals.

18. The neurostimulation system of claim 17, wherein the at least another of the electrical terminals is a plurality of electrical terminals.

19. The neurostimulation system of claim 17, wherein the analog output circuitry further comprises a current source configured for generating the electrical stimulation current.

20. The neurostimulation system of claim 19, wherein the control circuitry is further configured for modifying the total magnitude of the electrical stimulation current generated by the current source.

21. The neurostimulation system of claim 17, wherein the one or more variable resistors includes two or more variable resistors respectively associated with two or more of the electrical terminals.

22. The neurostimulation system of claim 17, further comprising telemetry circuitry configured for wirelessly receiving a control signal, wherein the control circuitry is configured for adjusting the one or more variable resistors in response to the control signal.

23. The neurostimulation system of claim 22, wherein the control signal designates at least two magnitude values for the electrical stimulation current at the at least two electrical terminals, and wherein the one or more variable resistors are adjusted to set the electrical stimulation current at the at least two electrical terminals respectively to the at least two magnitude values.

24. The neurostimulation system of claim 23, wherein the at least two magnitude values are fractionalized.

25. The neurostimulation system of claim 22, wherein the control signal designates one or more resistance values respectively for the one or more variable resistors, and wherein the control circuitry is configured for adjusting the one or more variable resistors respectively to the one or more resistance values.

26. The neurostimulation system of claim 17, further comprising monitoring circuitry configured for measuring one or more electrical parameters respectively associated with one or more of the at least two electrical terminals, wherein the control circuitry is configured for adjusting the one or more variable resistors in response to the one or more measured electrical parameters.

27. The neurostimulation system of claim 26, wherein the one or more electrical parameters comprises one or more magnitudes of current at the one or more electrical terminals.

28. The neurostimulation system of claim 26, wherein the one or more electrical parameters comprises one or more impedances at the one or more electrical terminals.

29. The neurostimulation system of claim 17, further comprising the array of electrodes.

30. The neurostimulation system of claim 17, further comprising a housing containing the plurality of electrical terminals, analog output circuitry, and control circuitry.

31. The neurostimulation system of claim 17, wherein the analog output circuitry comprises a current source that solely generates the electrical stimulation current.

* * * * *